United States Patent
Cipriani et al.

(10) Patent No.: US 6,621,085 B1
(45) Date of Patent: Sep. 16, 2003

(54) DEVICE FOR THE PRECISION ROTATION OF SAMPLES

(75) Inventors: Florent Cipriani, Claix (FR); Jean Charles Castagna, Sassenage (FR)

(73) Assignee: Europäisches Laboratorium für Molekularbiologie (EMBL), Heidelberg (DE)

( * ) Notice: Subject to any disclaimer, the term of this patent is extended or adjusted under 35 U.S.C. 154(b) by 0 days.

(21) Appl. No.: 09/868,646

(22) PCT Filed: Jan. 7, 2000

(86) PCT No.: PCT/EP00/00088
§ 371 (c)(1),
(2), (4) Date: Jun. 28, 2001

(87) PCT Pub. No.: WO00/40952
PCT Pub. Date: Jul. 13, 2000

(30) Foreign Application Priority Data

Jan. 7, 1999 (DE) .......................... 199 00 346

(51) Int. Cl.[7] .............................. G21K 5/10; H01J 37/00
(52) U.S. Cl. ............................... 250/442.11; 250/492.21
(58) Field of Search ....................... 250/440.11, 442.11, 250/492.21, 492.2

(56) References Cited

U.S. PATENT DOCUMENTS

| 4,064,657 A | * | 12/1977 | Habib | 451/123 |
| 4,771,178 A | * | 9/1988 | Egle et al. | 250/442.11 |
| 4,821,303 A | * | 4/1989 | Fawcett et al. | 378/80 |
| 5,786,600 A | * | 7/1998 | Lambert et al. | 250/484.4 |
| 5,898,179 A | * | 4/1999 | Smick et al. | 250/492.21 |
| 5,907,157 A | * | 5/1999 | Yoshioka et al. | 250/492.2 |
| 6,269,144 B1 | * | 7/2001 | Dube et al. | 378/71 |

FOREIGN PATENT DOCUMENTS

EP 0223297 5/1987

OTHER PUBLICATIONS

Patent Abstracts of Japan vol. 014, No. 169 (P–1032), Mar. 30, 1990.
Patent Abstract of Japan vol. 1999, No. 14, Dec. 22, 1999.

* cited by examiner

Primary Examiner—John R. Lee
Assistant Examiner—Paul M. Garzo
(74) Attorney, Agent, or Firm—Rothwell, Figg Ernst & Manbeck

(57) ABSTRACT

A device is proposed for the precision rotation of samples on a diffractometer, especially for X-ray or synchrotron radiation diffraction experiments, comprising:

Figure 1:
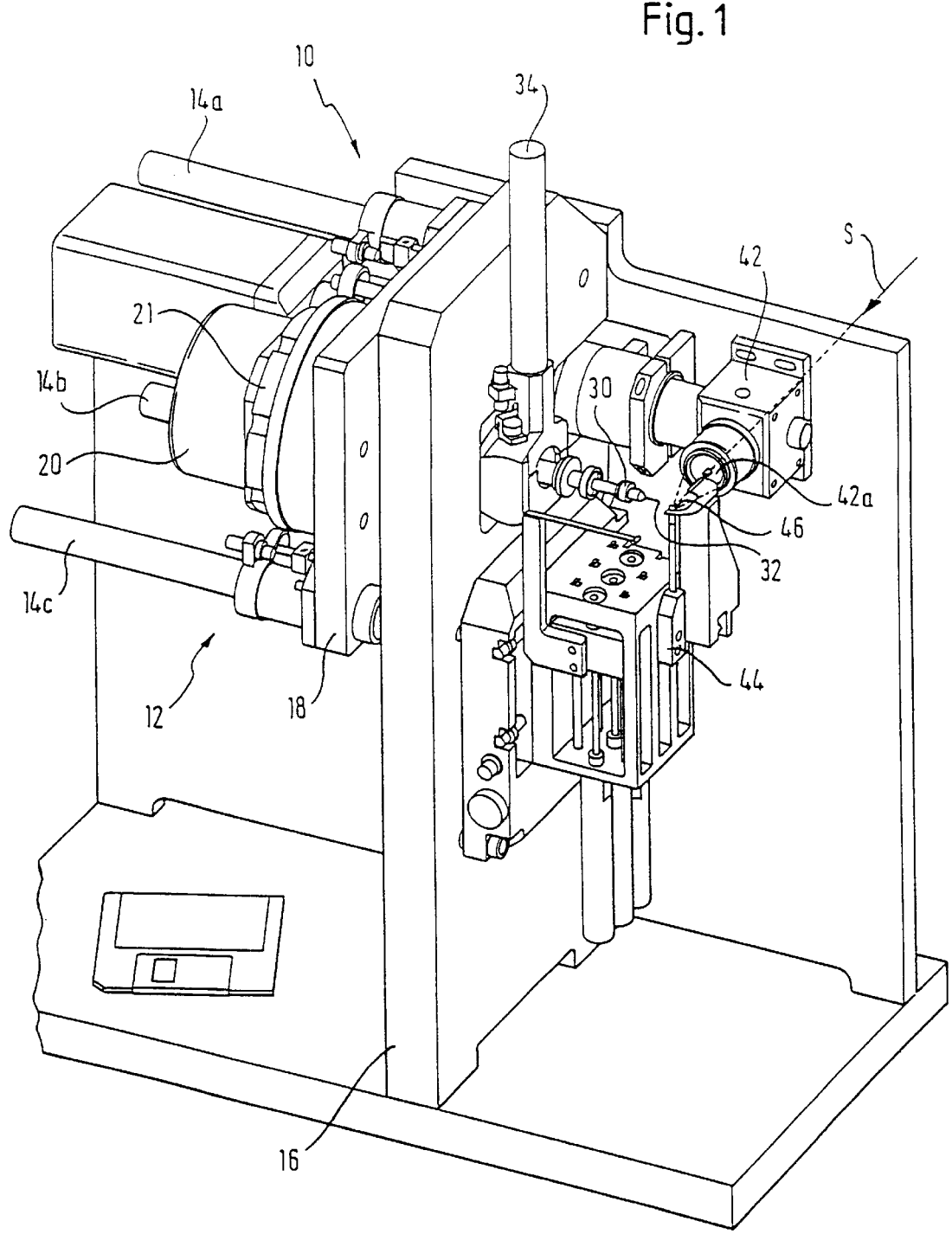

- a centering element (26) which is held at one end of a motor-driven rotating shaft (22) and can be displaced in a plane orthogonal to the axis of rotation of the rotating shaft (22),
- a sample holder (30) which is fixed to the centering element (26) or integral with the latter for holding a sample (32) substantially centrally with respect to the axis of rotation in an X-ray or synchrotron radiation beam (S),
- at least one micrometer finger (36) which is arranged in the region of the centering element (26) and can be positioned orthogonally with respect to the axis of rotation of the rotating shaft (22) by means of a micrometer finger drive device.

41 Claims, 6 Drawing Sheets

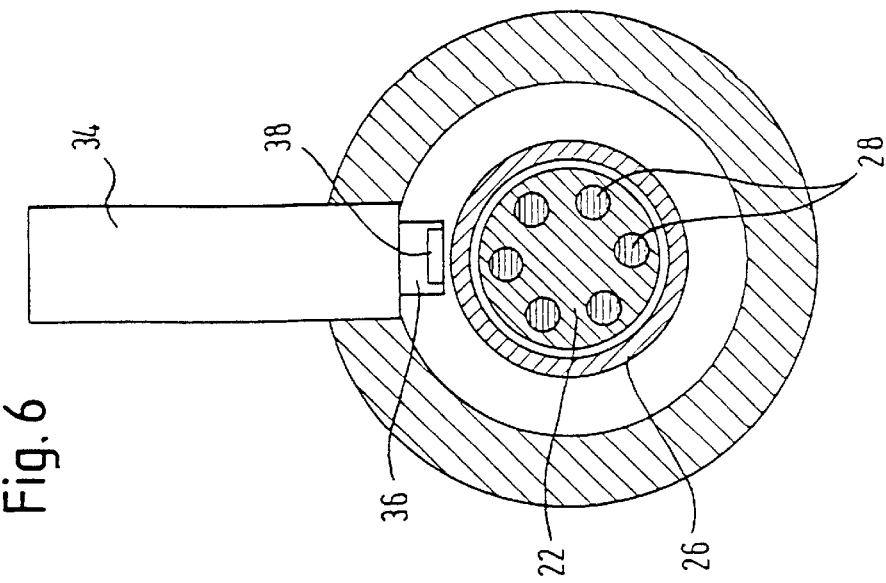
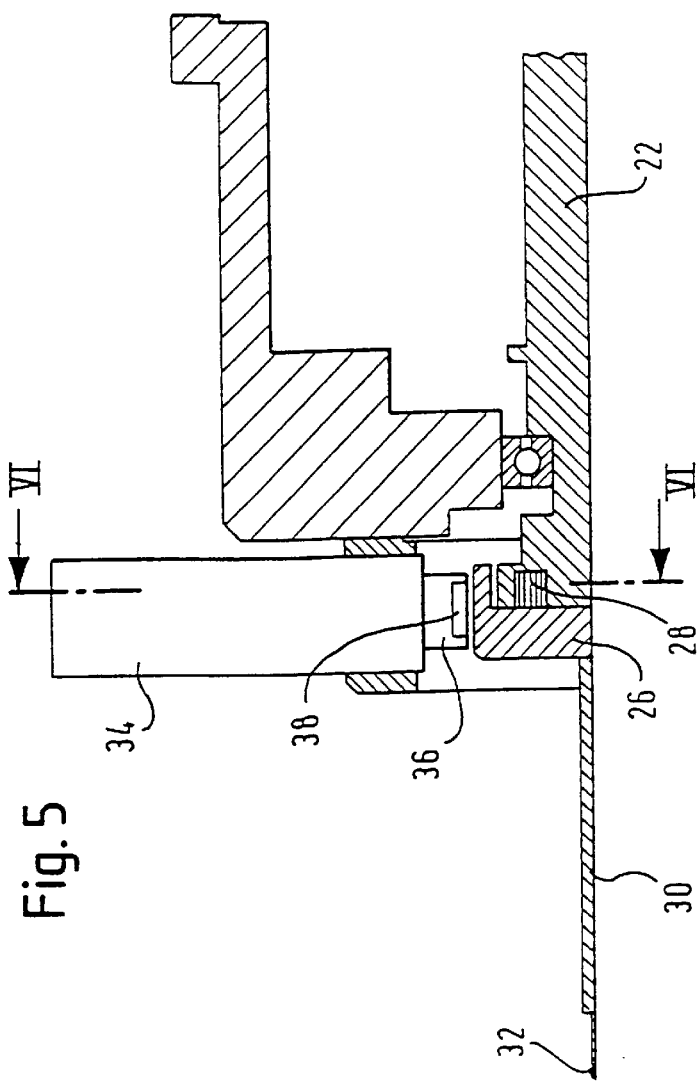
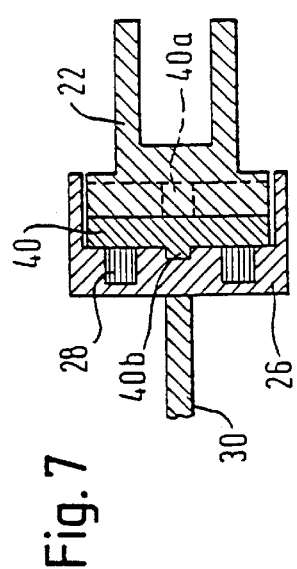

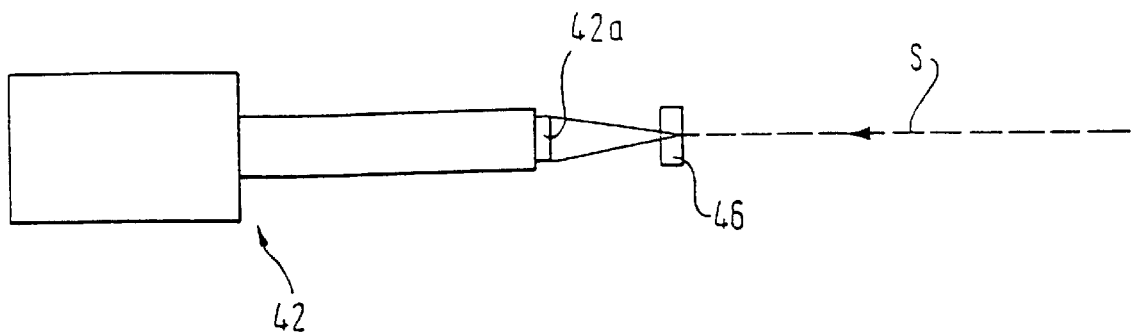
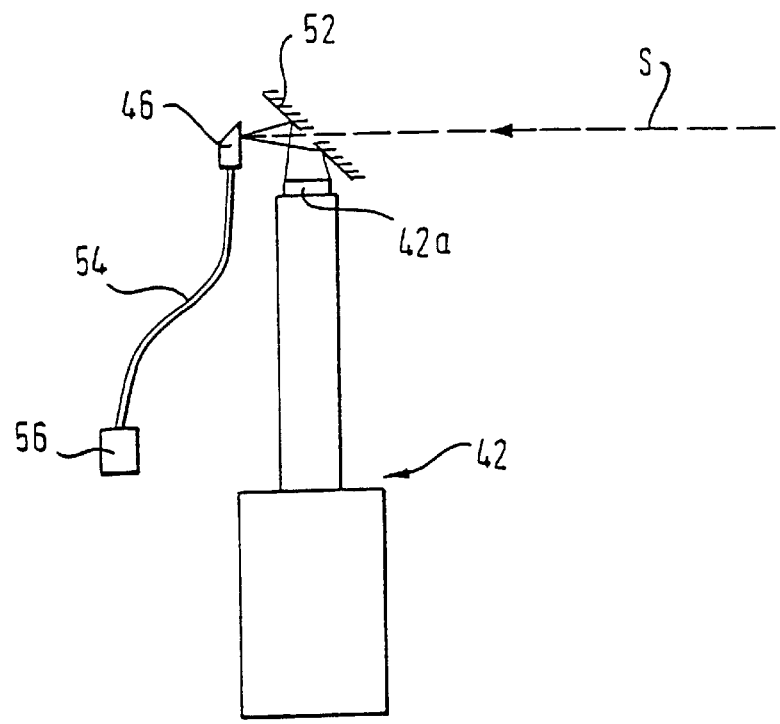

DEVICE FOR THE PRECISION ROTATION OF SAMPLES

Description

The present invention relates to a device for the precision rotation of samples on a diffractometer, in particular for X-ray or synchrotron radiation diffraction experiments.

The diffraction of X-ray is a method which has been known for a long time and is used worldwide for investigating the structure of condensed materials. In this case, a sample to be examined is introduced into an X-ray beam previously defined with regard to its wavelength distribution, its dimensions, its coherence properties and the like, and the intensity distribution of the X-radiation diffracted by the sample is investigated with the aid of an X-ray detector. Thus, for example, the static crystal structure of a solid body can be explained by measuring the position and the intensity of the Bragg signals diffracted elastically by it at an orientation to be determined precisely in relation to the incident X-ray beam in emergence directions which likewise have to be determined precisely.

In order to carry out such diffraction experiments on X-ray apparatus or, preferably, on modern synchrotron radiation sources, which are able to supply particularly high-energy X-rays, the sample is generally held by a sample holder which is fixed to a diffractometer. Such a diffractometer generally comprises a number of linear displacement and sample rotation devices, which can be motor-driven and therefore permit the adjustment of the sample and rotation of the sample in the beam, for example when looking for Bragg signals, in a measuring cubicle which is generally not accessible to the experimenters for reasons of safety during measurement operations. In order to carry out the measurements, it is important that the sample is arranged in the beam as exactly centrally as possible in relation to the axis of rotation of the rotating shaft. This is because, otherwise, in the event of rotation of the rotating shaft, an additional displacement of the sample in the beam can occur. It is precisely in the case of biological samples, which frequently can be produced only with dimensions of the order of magnitude of 1 $\mu$m and for the examination of which X-ray or synchrotron radiation and beams with correspondingly small dimensions transverse to the propagation direction are used, that such centering is important, since the sample otherwise can even be rotated out of the beam during rotation of the rotating shaft.

For this reason, in the construction of diffractometers it is generally known to fix an additional displacement device, often referred to as an XY table, to the device for rotating the samples, said device comprising two linear displacement units which can be displaced orthogonally with respect to each other, generally by means of a motor. By means of the generally iterative adjustment of these two linear displacement units, the sample can be positioned substantially centrally in relation to the axis of rotation.

However, in the case of examining the aforementioned biological samples with typical dimensions of the order of magnitude of 1 $\mu$m, a device for rotating samples which is configured in this way exhibits disadvantages. For example, the motors which drive such linear displacement units are provided with cables which, during each rotation or displacement of the sample, exert a tensile stress on the end of the rotating shaft on the sample side. This can lead to the shaft being bent at the end on the sample side or the entire shaft, which has a certain amount of play, being displaced, so that the sample runs out of the axis of rotation and/or out of the beam. Furthermore, the motor cables that belong to the linear displacement units and corotate with the device for rotating samples hamper the free rotatability of the device for rotating samples and can even inadvertently be torn off if they wind around the device for rotating samples during the rotation of the sample. If, in order to avoid cables, the motor drive to the displacement units of the XY table is dispensed with and if said displacement units are adjusted manually instead, then the time required for the sample adjustment increases sharply, in particular in the case of synchrotron beam sites, because of the safety regulations when entering and leaving the measurement cubicle. In addition, in manually adjustable displacement units, the problem also occurs that their weight loads the rotating shaft, in particular in the case of horizontally mounted rotating shafts, which likewise can lead to the above-described bending or displacement of the rotating shaft.

It is therefore an object of the invention to propose a device for rotating samples on a diffractometer of this kind which permits the sample to be positioned in the beam simply, quickly and continuously during measurement operation.

According to the invention, this object is achieved by a device for the precision rotation of samples on a diffractometer, especially for X-ray or synchrotron radiation diffraction experiments, comprising:

a centering element which is held at one end of a motor-driven rotating shaft and can be displaced in a plane orthogonal to the axis of rotation of the rotating shaft, a sample holder which is fixed to the centering element or integral with the latter for holding a sample substantially centrally with respect to the axis of rotation in an X-ray or synchrotron radiation beam, at least one micrometer finger which is arranged in the region of the centering element and can be positioned orthogonally with respect to the axis of rotation of the rotating shaft by means of a micrometer finger drive device.

In order to position the sample substantially centrally with respect to the axis of rotation, the centering element, to which the sample holder holding the sample is fixed or with which it is integral, is attached to that end of the motor-driven rotating shaft which is provided for this purpose. In this case, the sample is generally not arranged centrally with respect to the axis of rotation of the rotating shaft. This can be detected from the fact that the sample or its center does not remain in a fixed position during rotation of the rotating shaft. Instead, the sample will run through a circular path during rotation of the rotating shaft through 360°. The center of this circular path identifies the axis of rotation of the rotating shaft. With the aid of the micrometer finger, the centering element can now be displaced with respect to the rotating shaft to such an extent that the sample is located at the center of the circular path previously observed, and therefore centrally with respect to the axis of rotation.

In practice, the procedure is, for example, as follows: after the centering element has been attached to the rotating shaft, the latter is rotated through 360° and the radius r of the circular path described by the sample in this case is measured. The rotating shaft is then rotated into a rotational position in which the orientation of the sample relative to the center of the circular path corresponds to the orientation of the micrometer finger relative to the centering element. If, for example, the micrometer finger in the laboratory system is arranged above the centering element, then the rotating shaft is rotated into a position in which the sample is arranged above the center of the circular path. The micrometer finger is then displaced, downward in the aforementioned example, until the sample is arranged centrally in relation to the center of the circle and therefore in relation to the axis of rotation. Following such positioning of the sample, the micrometer finger may possibly be withdrawn again by its drive device, in order not to hamper the free rotation of the rotating shaft. Since, as opposed to conventional diffractometers, in the case of the device for the precision rotation of samples according to the invention no heavy, generally motorized, displacement devices are attached to the rotating shaft, but instead only a centering element, which can substantially be designed as a disk and which can be displaced by the micrometer finger arranged outside the rotating shaft, the rotating shaft is free of tensile stresses and substantially free of weight loads, so that the sample can be permanently positioned with micrometer accuracy centrally in relation to the axis of rotation.

At the beginning of the displacement of the centering element relative to the rotating shaft with the aid of the initially withdrawn micrometer finger that can be positioned orthogonally with respect to the axis of rotation, in order to permit this micrometer finger to be placed as gently as possible on the centering element, a device for detecting the instantaneous clear distance, or possibly zero distance, between the micrometer finger and the centering element can be provided. It is possible for the speed of the micrometer finger drive device to be controlled on the basis of the instantaneous clear distance, detected by the detection device, between the micrometer finger and the centering element. This control will expediently be performed in such a way that the speed of the micrometer finger drive device is reduced as the clear distance decreases.

In an embodiment which is simple to implement, provision is made for the detection device to comprise a capacitance sensor arranged at the end of the micrometer finger facing the centering element. Such capacitance sensors are known in metrology and permit the determination of a distance between two components forming an electrical capacitor with a resolution of generally less than 1 $\mu$m. On the basis of the clear distance detected in this way, it is possible to reduce the speed of the micrometer finger drive device continuously until the zero distance is reached, that is to say contact between the micrometer finger and the centering element, or the micrometer finger drive device can move the micrometer finger toward the centering element at a first, high speed until a safety margin is reached, for example of the order of magnitude of 10 $\mu$m, and when the distance falls below this safety margin, change over to a second, lower speed until the zero distance is reached.

In order to be able to displace the centering element with the aid of the micrometer finger in a plane orthogonal to the axis of rotation of the rotating shaft, the invention preferably provides for the centering element to be held magnetically on the rotating shaft. The magnetic force needed for this purpose between the centering element and the rotating shaft can be effected in a simple way by one or more permanent magnets being led into the end of the rotating shaft or into the centering element, and the respective other end being at least partly produced from ferromagnetic material, for example iron. In principle, of course, the use of electromagnets to produce the magnetic force is also possible.

In order to be able to monitor the rotation of the shaft as well as possible during the initial adjustment and during the subsequent performance of diffraction experiments, in the case of the device for the precision rotation of samples according to the invention, provision can be made for it to comprise an encoder for determining the rotational position of the rotating shaft, possibly an electric motor driving the rotating shaft. The use of such encoders on diffractometers for detecting the rotational positions of rotating shafts or electric motors is known and can permit these rotational positions to be determined with a resolution of down to 1/1000 degree.

For the micrometer finger drive device, various configurations are possible: in a simple embodiment of the device for the precision rotation of samples according to the invention, provision is made for the micrometer finger drive device to comprise an electrically driven linear displacement unit. This embodiment has the advantage that the linear displacement unit belonging to the micrometer finger drive device can generally easily be integrated into the existing diffractometer control system, since it is most often the case that further such linear displacement units are provided in any case.

Alternatively, however, it is also possible for the micrometer finger drive device to comprise a piezoelectric crystal. The expansion or contraction of a piezoelectric crystal, controlled by means of an external voltage, permits very accurate positioning of the micrometer finger and, for this purpose, substantially requires no mechanical, wear-susceptible components.

Alternatively, however, it is also possible for the micrometer finger drive device to comprise a coil through which current flows within a magnetic field. In addition, a space-saving construction of this type, which is known from loudspeakers, for example, permits accurate positioning of the micrometer finger without the use of wear-susceptible components.

During the displacement of the centering element, envisaged by the invention, by means of the micrometer finger which can be positioned orthogonally with respect to the axis of rotation, it may occur that the centering element is not arranged exactly centrally in relation to the direction of movement of the micrometer finger. The displacement of the centering element that is effected by the micrometer finger then exhibits a rotation in addition to the actually desired translation, that is to say rectilinear displacement. It is therefore possible for the sample not to be arranged precisely centrally with respect to the axis of rotation, even after this displacement, which can be determined by a monitoring rotation of the rotating shaft, generally carried out after this adjustment step, since the sample then again runs on a circular path, although its radius is generally substantially smaller than the radius of the circular path observed before this adjustment step. In order largely to avoid the occurrence of the aforementioned undesirable rotation of the sample, and therefore to reduce the number of adjustment steps which are required to position the sample centrally in relation to the axis of rotation, a development of the device for the precision rotation of samples according to the invention provides that, between the centering element and the end of the rotating shaft there is provided a guide disk, preferably a round guide disk, which extends substantially orthogonally with respect to the rotating shaft, the end of the rotating shaft, the guide disk and the centering element having guide means such that the centering element can be displaced with respect to the guide disk only in a first direction, and the guide disk can be displaced with respect to the rotating shaft only in a second direction orthogonal to the first direction. It is then possible to break down the requisite displacement of the centering element, derived from the first circular path through which the not yet adjusted sample passes, into two mutually orthogonal displacements which are carried out in two rotational position of the rotating shaft which are offset by 90° from each other, in which positions the guide means ensure that during one, for example the first displacement, only the centering element is displaced relative to the guide disk and that during the other, for example the second displacement, only the guide disk with the centering element arranged on it is displaced relative to the rotating shaft.

A practical implementation of this embodiment can be carried out by the guide means comprising pins fixed to the guide disk on the rotating shaft side and on the centering element side and substantially at the center of said disk, and also grooves, at the end of the rotating shaft and in the region of the centering element on the guide disk side, to accommodate the pins, the grooves extending orthogonally with respect to each other and orthogonally with respect to the rotating shaft when the guide means are fitted. A configuration of this type offers the advantage of simple manufacture. In the case of this embodiment, it is of course also possible for the permanent magnets needed for the magnetic holding action to be provided in the guide disk.

As mentioned above, the sample holder can be formed integrally with the centering element. Since, on synchrotron radiation sources, because of the generally only short available measurement times, the intention is that no valuable "beam time" is to be lost at a sample change as a result of the attachment of a new sample to the sample holder previously used, but instead that sample holders generally previously fitted with samples are to be placed on the diffractometer quickly, it is advantageous, for reasons of measurement time and costs, if the sample holder with the centering element is fixed detachably. This can be effected by the sample holder being held on the centering element by vacuum which is generated by a pump device connected to the centering element. Such "attachment by vacuum" of a sample holder fitted with a sample to a diffractometer, or else the attachment by vacuum of a sample to a sample holder is known from numerous measurement sites for diffraction experiments and permits a quick sample change.

In order to simplify the sample adjustment further, in a device for the precision rotation of samples according to the invention, provision can be made for it also to contain an optical device for detecting the position of the beam and the position of the sample, comprising a scintillator that can optionally be set up at the sample location, and a video microscope aimed at the sample location. In this case, the position of the beam can be detected in that, with the sample not yet installed or moved away by the diffractometer, the scintillator set up at the sample location emits flashes of light at the point of incidence of the beam under the action of the X-ray or synchrotron radiation beam. These flashes of light can be observed with the video microscope aimed at the sample location and permit the localization of the beam position, for example in a coordinate system on a monitor connected to the video microscope. The scintillator is then removed from the sample location and the sample is installed and/or displaced to the sample location again with the aid of the diffractometer. The video microscope then facilitates the above-described centering of the sample with regard to the axis of rotation, in that it permits the observation, in an enlargement on the monitor, of the circular path described by the not yet adjusted sample during rotation of the rotating shaft. Following this adjustment, the video microscope also permits rapid positioning of the adjusted sample in the beam, since it is able to display the sample continuously on the monitor into whose coordinate system the beam position was entered at the start.

This introduction of the adjusted sample into the beam can be carried out by the rotating shaft and the components connected to it being fixed to a diffractometer table or a motorized tilting device. Such diffractometer tables, which can have a plurality of linear displacement and rotation devices, and such motorized tilting devices, in which generally at least three telescopic legs which can be extended and retracted are provided, are known per se and will not be explained specifically here.

In an advantageous development of the invention, provision is made for the scintillator to be fixed to a motorized displacement table. In this way, the scintillator can be moved into and out of the beam without the measuring cubicle having to be entered and therefore measurement time being lost.

In an advantageous development of the invention, provision is made for the scintillator to be coupled to a photodiode by means of an optical waveguide. Such a configuration permits the scintillator to be used not only for generating the flashes of light to be observed with the video microscope but, at the same time, also to utilize a relationship between the amount of light generated by it and the intensity of the incident beam and therefore to use it for measuring the beam intensity.

In principle, it is possible to set up the video microscope aimed at the sample location at any position which permits the sample location to be observed. However, in an advantageous embodiment of the invention, provision is made for the video microscope to be aimed at the sample location coaxially with respect to the beam. This observation of the sample carried out coaxially with respect to the beam permits the particularly trouble-free and quick positioning of the sample in the beam, since in this geometry no parallax errors occur. Reference is made to the fact that in the case of observing the sample coaxially with respect to the beam, it is not the entire circular path through which the sample passes during the adjustment, but essentially only its projection on the plane of the objective of the video microscope, which is visible. Therefore, during the observation "from the side" carried out coaxially with respect to the beam, instead of the circular path, it is only the upward and downward movement of the unadjusted sample which is seen. The determination of the radius of the circular path as half the distance between the two "extreme positions" of the sample is possible without problems in this case.

Setting up the video microscope in this way can simply be carried out by the video microscope being arranged in the forward direction in extension of the beam. In this case, for the purpose of adjustment, the video microscope is arranged in the region of the X-ray detector used for the measurement.

In an advantageous alternative embodiment of the invention, in which the video microscope can remain in operation even during the measurements, provision is made for the video microscope to be aimed, with an orientation of 90° with respect to the beam, at a mirror which is oriented at 45° with respect to the beam and is penetrated by the latter through a hole provided in the mirror. This embodiment offers the advantage that the mirror can be removed quickly, for example during the sample change, and can then be installed again, which facilitates the sample changing and other operations on the device for the precision rotation of samples according to the invention.

Alternatively, however, it is also possible for the objective of the video microscope to be provided with a coaxial hole, through which the beam runs before reaching the sample.

This configuration permits the objective of the video microscope to be arranged very close to the sample, which is advantageous in the case of particularly small samples which are difficult to detect.

A further lightening of the work with the device for the precision rotation of samples according to the invention is possible if the image registered by the video microscope is fed to a computer for automatic beam localization and sample adjustment. It is then possible, for example, for the image registered by the video microscope to be displayed on the same computer monitor as a diffractometer control program that controls the operation of the diffractometer. Given appropriate programming, it is even possible to automate the beam localization, the actions of moving the scintillator into and out of the beam needed for this purpose, the adjustment of the sample centrally with respect to the axis of rotation and/or moving the adjusted sample into the beam. In this way, the previously generally tiresome and time-consuming adjustment can be simplified and accelerator.

In a development of the sample rotation device according to the invention, provision can be made for it to comprise further motorized displacement tables for the introduction of beam stops, beam tubes and the like into the beam. The use of such beam stops, for example in the form of lead disks, to protect the detector from the beam during the adjustment, and also the use of beam tubes, for example in the form of small molybdenum tubes open at their longitudinal ends in order to limit the background signal caused by air scattering, is known per se in X-ray and synchrotron radiation experiments.

In the sample rotation device according to the invention, provision is expediently made for it also to comprise means for attaching a sample surround, for example a cooling, heating or magnetizing device. In the simplest case, means of this type for attaching sample surrounds comprise a regular arrangement of threaded holes, such as are known, for example, from conventional linear displacement and rotation devices for diffractometers.

Of course, the sample rotation device according to the invention is able better to ensure a permanently stable position of the sample to the beam if, in addition to the above-described adjustment of the sample centrally with respect to the axis of rotation, the stability of this axis of rotation relative to the beam is also ensured. This requires the most stable mounting of the rotating shaft. For this reason, provision can be made for the rotating shaft to be mounted using ball bearings.

Alternatively, however, it is also possible for the rotating shaft to be mounted using air bearings. In the case of such air bearings, the rotating shaft is accommodated in a cylindrical depression in a bearing housing and is acted on with compressed air through openings in the wall of this cylindrical depression in such a way that it can rotate freely without any frictional contact with the wall of the depression. The positional stability of shafts mounted in this way is generally higher than that which can be achieved with ball bearings.

Figure 2:
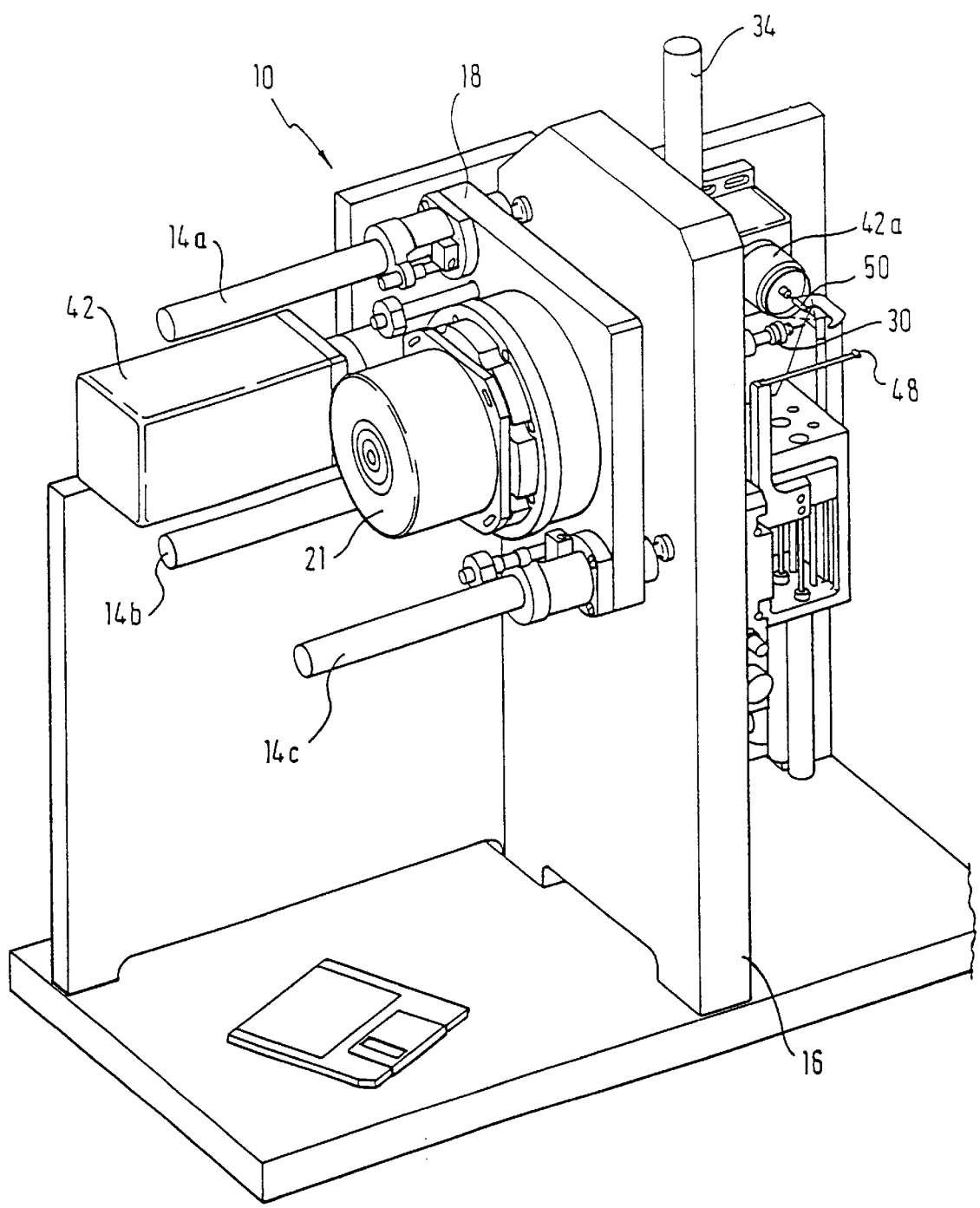
Figure 3:
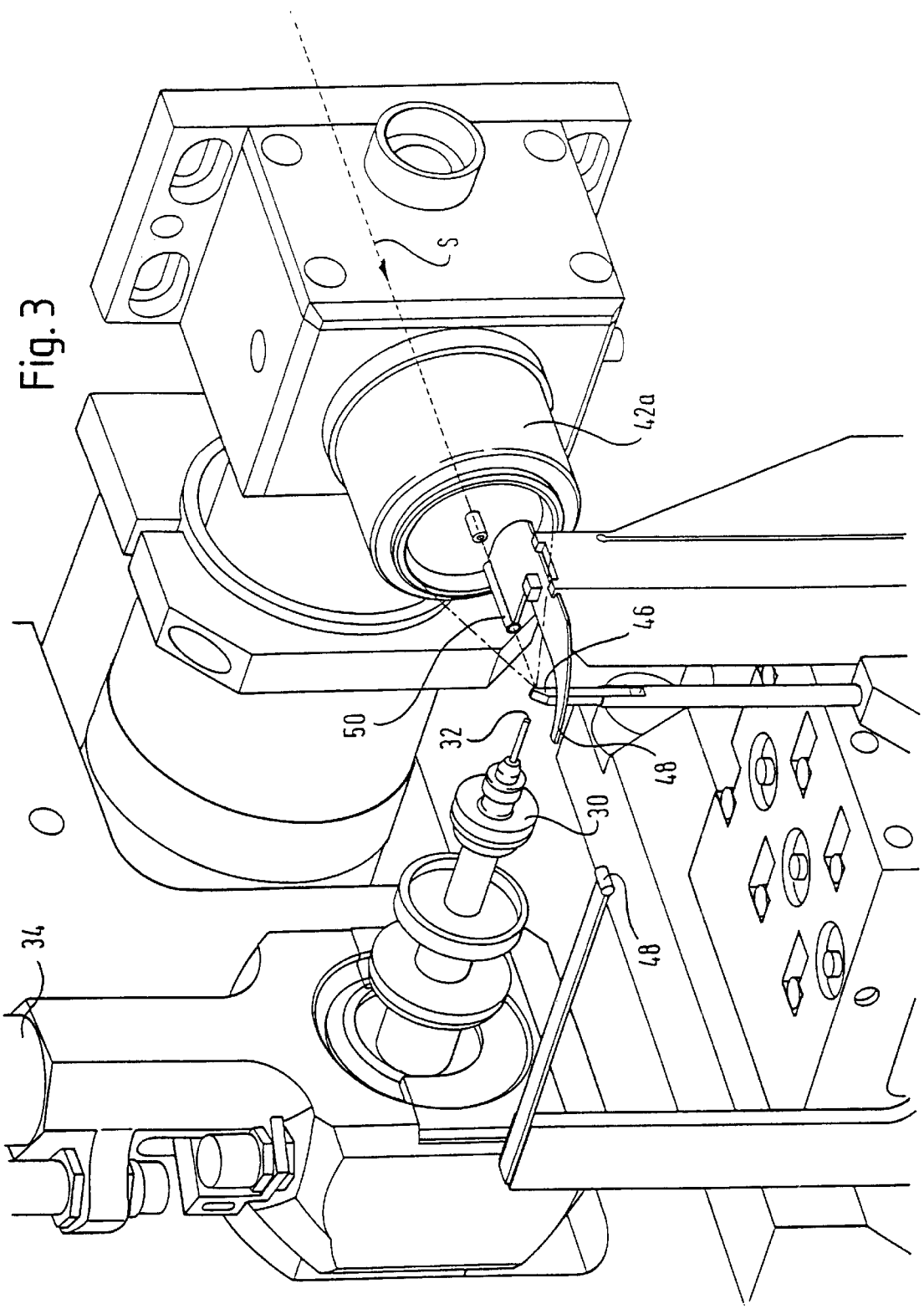
Figure 4:
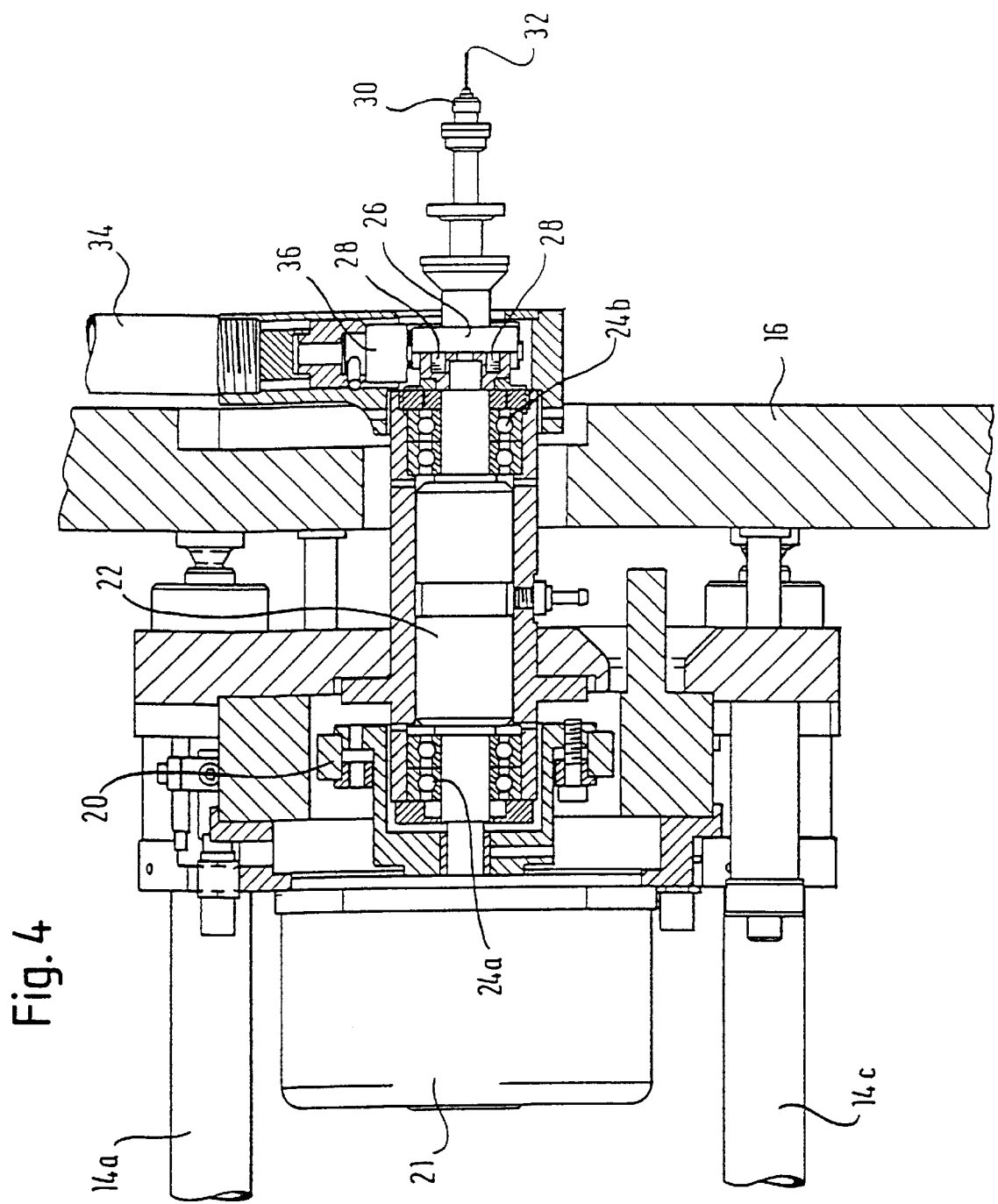

The invention will be explained below using a preferred exemplary embodiment and the drawing, in which:

FIG. 1 shows a perspective view of a first embodiment of the device for the precision rotation of samples according to the invention, with the sample and the beam in the foreground, FIG. 2 shows a perspective view of the first embodiment according to FIG. 1, with the motorized tilting device in the foreground, FIG. 3 shows an enlarged detail of the sample area of the perspective view according to FIG. 1, FIG. 4 shows a schematic, sectioned side view of the first embodiment of the device for the precision rotation of samples according to the invention, FIG. 5 shows a schematic, enlarged detail of the area of the centering element and of the micrometer finger from FIG. 4, FIG. 6 shows a front view of the section along the line VI—VI in FIG. 5, FIG. 7 shows a schematic illustration of the guide disk provided between the centering element and the end of the rotating shaft in a second embodiment of the invention, FIG. 8 shows a schematic illustration of the positioning of the video microscope in a third embodiment of the invention, FIG. 9 shows a schematic illustration of the positioning of the video microscope in a fourth embodiment of the invention.

As can be seen in the overall view of FIGS. 1 and 2, the device 10 for the precision rotation of samples according to the invention comprises a motorized tilting device 12 having telescopic legs 14a, b, c which can be extended and retracted by motors. Their free ends are fixed to a vertical holding plate 16, while the telescopic elements of the telescopic legs 14a, b, c, which can be displaced with respect to these free ends by motors, pneumatically or in a similar way, carry a housing 18. This housing 18 and the parts connected to it can thus be tilted with respect to the vertical holding plate 16 by optionally extending or retracting at least one or more of the telescopic legs 14a, b, c.

Fixed in the housing 18 is an electric motor 20, which drives a rotating shaft 22 which penetrates the vertical holding plate 16 through a hole provided in the latter. The rotating shaft 22 is mounted using ball bearings 24a, 24b. Instead of the ball bearings 24a, b, air bearings could optionally also be used. An encoder 21 fixed to the housing 18 detects the rotational position of the electric motor 20, so that deviations between the desired and actual rotational positions of the motor 20 can be corrected if necessary.

At that end of the rotating shaft 22 facing away from the electric motor 20, a centering element 26 is held magnetically. This magnetic holding action is ensured by the centering element 26 being produced from a ferromagnetic material, for example iron, and permanent magnets 28 being let into the end of the rotating shaft 22. In this way, the centering element is held in a stable manner and can nevertheless be displaced in the contact plane between the rotating shaft 22 and the centering element 26.

At the end of the centering element 26 facing away from the rotating shaft 22, a sample holder 30 is fixed, and holds a sample 32. To this end, the sample 32 is, for example, adhesively bonded to the sample holder 30. The sample holder 30 is preferably fixed to the centering element 26 by means of vacuum, which is generated by a pump device which is connected to the centering element 26 but not shown in the figures. This vacuum method for holding samples or sample holders is known per se in diffractometers for diffraction experiments.

In order to be able to adjust the sample 32 centrally with respect to the axis of rotation of the rotating shaft 22 in the X-ray or synchrotron radiation beam S indicated by a dashed line in FIGS. 1 and 3, a micrometer finger 36 which can be positioned orthogonally with respect to the axis of rotation of the rotating shaft 22 in a guide housing 34 is arranged above the centering element 26. By means of a drive which is not shown in the figures, for example an electrically driven linear displacement unit, a piezoelectric crystal or a coil through which current flows within a magnetic field, the micrometer finger 36 can be moved downward from above toward the centering elements 26 and, after coming into contact with the centering element 26, can displace the latter downward by a distance which substantially corresponds to the radius of the circular path described by the not yet adjusted sample during rotation of the rotating shaft 22 through 360°. During the approach of the micrometer finger 36 to the centering element 26, in order to be able to detect the clear distance between the two parts, a capacitance sensor 38 is arranged in the end of the micrometer finger 36 on the centering element side, as can be seen in particular in FIGS. 5 and 6. It goes without saying that the micrometer finger 36 can, for example, also be arranged under the centering element 26, in order possibly to displace the latter upward, and that the micrometer finger 36, in the front view shown in FIG. 6, can even assume any desired angular position in which it can be positioned orthogonally with respect to the axis of rotation of the motor 20 toward and away from the centering element 26. If necessary, it is even possible for a plurality of micrometer fingers 36 arranged in this way to be provided.

As can be seen in the front view shown in FIG. 6, the micrometer finger 36 can be positioned substantially centrally in relation to the centering element 26. When the centering element 26 is displaced, downward in FIG. 6, with the aid of the micrometer finger 36, the centering element 26 should therefore execute the desired rectilinear movement. If the micrometer finger 36 is not placed exactly centrally on the centering element 26, however, the displacement which is executed may include undesired rotation of the centering element 26, and fail to achieve the intended adjustment of the sample. For this reason, in a second embodiment of the invention, between the centering element 26 and the end of the rotating shaft 22 there is provided a round guide disk 40 which extends substantially orthogonally with respect to the rotating shaft 22. As can be seen in FIG. 7, the guide disk 40 has a pin 40a on the rotating shaft side and a pin 40b on the centering element side, each of which is arranged at the center of said disk. The pin 40a on the rotating shaft side runs in a groove formed in the end of the rotating shaft 22, said groove extending in the plane of the drawing in FIG. 7 and being indicated dashed. This ensures that the guide disk 40 can be displaced relative to the rotating shaft 22 only upward or downward in FIG. 7. The pin 40b on the centering element side is accommodated in a groove formed in the end of the centering element 26 on the guide disk side, said groove extending orthogonally with respect to the plane of the drawing in FIG. 7. This ensures that the centering element 26 can be displaced relative to the guide disk 40 only orthogonally with respect to the plane of the drawing in FIG. 7. If, in this embodiment, the micrometer finger 36 is used to displace the centering element 26 only into such rotational positions of the rotating shaft 22 in which one of the two grooves is oriented parallel to the displacement direction of the micrometer finger 36, and the other groove consequently orthogonally to this displacement direction, then it is possible for the above-described undesired rotation of the centering element 26 to be avoided during the displacement.

As can be seen in FIGS. 1 to 3, in the first embodiment of the device for the precision rotation of samples according to the invention, the objective 42a of the video microscope 42 is provided with a hole through which the beam S indicated dashed in FIG. 3 runs. This arrangement permits the sample location to be observed coaxially with respect to the beam S.

In the arrangement shown in FIG. 3, the video microscope 42 is currently being used to detect the position of the beam S. For this purpose, a scintillator 46 fixed to a motorized displacement table 44 has been moved to the sample location, after the sample 32 has been withdrawn from this position with the aid of the motorized tilting device 12. The scintillator 46 which is struck by the beam S and which, for example, can be produced from $Bi_4Ge_3O_{12}$, from $CdWO_4$ or another scintillator material, then emits light which, as indicated by a schematic cone of light in FIG. 3, is registered by the objective 42a of the video microscope 42. This permits the point of incidence of the beam S on the scintillator 46 to be displayed in a coordinate system on a monitor, in particular a computer monitor, which is connected to the video microscope 42.

In order to look after the X-ray detector, which is not needed during this detection of the beam position, two beam stops 48 can also be moved into the beam S together with the scintillator 46. In FIG. 3, there is also fixed to the holder of the first beam stop 48 in the beam direction a small molybdenum beam tube 50 which is open at its ends and through which the beam S runs before reaching the scintillator 46, in order in particular to protect the objective 42a against air-scattered X-ray or synchrotron radiation beams.

In the embodiment shown in FIG. 3, in which an objective 42a provided with a hole is used, it goes without saying that, upstream of this objective 42a, there is arranged a mirror which is substantially oriented at 45° with respect to the beam and is provided with a hole for the beam and which reflects the light registered by the objective 42a to the actual camera part of the video microscope 42.

After the detection of the beam position, carried out in this way, the scintillator 46 is moved away downward in FIG. 3 with the aid of its motorized displacement table 44 and, with the aid of the motorized tilting device 12, the still unadjusted sample 32 is moved to the position previously assumed by the scintillator 46. In the arrangement of the video microscope 42 shown in FIG. 3, the latter is used to observe, during the rotation of the rotating shaft 22 through 360°, the projection of the circular path described by the sample 32 onto the plane of the objective 42a, that is to say the upward and downward movement of the sample 32 is observed. The spacing between the topmost and the lowest point of this upward and downward movement of the sample 32 corresponds to the diameter of the circular path. Observing the sample 32 with the aid of the video microscope 42 therefore permits the determination of the distance through which said sample is offset with respect to the axis of rotation of the rotating shaft 22. The rotating shaft 22 is then rotated into a rotational position in which the sample 32 is arranged at the topmost point of the observed upward and downward movement, and the centering element 26 is then displaced downward with the aid of the micrometer finger 36 by the requisite distance, namely by the radius of the circular path. For reasons of safety, another rotation of the rotating shaft 22 through 360° will then be carried out, and the path described by the probe in this case will be observed and, if necessary, a renewed correction will be carried out. Experience shows that such iterative adjustment steps converge very quickly, so that the adjusted sample is ultimately in a stable position during rotation of the rotating shaft 22.

FIGS. 8 and 9 show, in schematic form, other positioning possibilities for the video microscope 42 in further embodiments of the invention.

In FIG. 8, the video microscope 42 is arranged in the forward direction in direct extension of the beam S striking the scintillator 46. An arrangement of this type can be selected, for example, if already existing diffractometers are to be retrofitted with a video microscope 42, for which no other set-up position can be found for reasons of space. In the arrangement shown in FIG. 8, following the detection of the beam position, the centering of the sample 32 and the action of moving the sample 32 into the beam S with the aid of the motorized tilting device 12, the video microscope 42 has to be moved in order to be able to examine the diffraction signals produced by the sample 32.

By contrast, in the arrangement shown schematically in FIG. 9, the video microscope 42 can also remain installed and in operation during the measurements. This is because in this case the video microscope 42 is aimed, at 90° with respect to the beam S, at a mirror 52 which is oriented at 45° with respect to the beam S and allows the latter through a hole provided in the mirror 52. The light beam path indicated in FIG. 9 makes it clear that the video microscope 42 is aimed at the sample location, coaxially with the beam, in this arrangement as well.

In FIG. 9, the scintillator 46 is connected via an optical waveguide 54 to a photodiode 56 or the like, which permits quantitative checking of the intensity of the beam S. It is therefore possible, as early as when detecting the position of the beam, to check whether the components arranged upstream of the beam and belonging to the measuring system or the X-ray system or the synchrotron itself are functioning properly.

The device for the precision rotation of samples according to the invention and described permits, in general terms, exact positioning of a sample centrally in relation to an axis of rotation. This application to a diffractometer is not restricted to the X-ray or synchrotron diffraction experiments cited by way of example, but can in principle also be used on diffractometers for neutron scattering and other scattering experiments. In this case, it goes without saying that the device 10 for the precision rotation of samples according to the invention can be combined with further linear displacement and/or rotation devices. For example, it is possible to fix the construction shown in FIGS. 1 to 3 to an already existing diffractometer. Furthermore, those skilled in the art in the field of diffractometers for diffraction experiments will see that there are numerous possibilities of replacing the above-described components of the device 10 for the precision rotation of samples according to the invention by equivalent components. For example, the motorized tilting device 12 can be replaced by a combination of a conventional lifting table and a plurality of conventional Euler balances, that is to say a combination of linear displacement and rotation devices. Likewise, it is possible not to hold the centering element 26 on the rotating shaft 22 magnetically but instead, in a manner similar to holding the sample holder 30 on the centering element 26 as described, by means of a vacuum exerted by the end of the rotating shaft 22. A fastening of this type also permits displacement of the centering element 26 relative to the rotating shaft 22 in the plane of contact between these two components.

What is claimed is:

1. A device for the precision rotation of samples on a diffractometer, comprising:
    a centering element which is held at one end of a motor-driven rotating shaft and can be displaced in a plane orthogonal to the axis of rotation of the rotating shaft, a sample holder$_2$ which is fixed to the centering element or integral with the latter and which moves with the centering element when the centering element is displaced in the plane orthogonal to the axis of rotation of the rotating shaft, for holding a sample substantially centrally with respect to the axis of rotation in an X-ray or synchrotron radiation beam,
    at least one micrometer finger arranged in the region of the centering element in order to displace the centering element in a plane orthogonal to the axis of rotation of the rotating shaft, wherein the micrometer finger can be positioned orthogonally with respect to the axis of rotation of the rotating shaft by means of a micrometer finger drive device.

2. The device for the precision rotation of samples as claimed in claim 1, further comprising a device for detecting the instantaneous clear distance, or possibly zero distance, between the micrometer finger and the centering element.

3. The device for the precision rotation of samples as claimed in claim 2 characterized in that the detection device comprises a capacitance sensor arranged at the end of the micrometer finger facing the centering element.

4. The device for the precision rotation of samples as claimed in claim 1, characterized in that the centering element is held magnetically on the rotating shaft.

5. The device for the precision rotation of samples as claimed in claim 1 further comprising an encoder for determining the rotational position of the rotating shaft.

6. The device for the precision rotation of samples as claimed in claim 1 characterized in that the micrometer finger drive device comprises an electrically driven linear displacement unit.

7. The device for the precision rotation of samples as claimed in claim 1 characterized in that the micrometer finger drive device comprises a piezoelectric crystal.

8. The device for the precision rotation of samples as claimed in claim 1 characterized in that the micrometer finger drive device comprises a coil through which current flows within a magnetic field.

9. The device for the precision rotation of samples as claimed in claim 1 characterized in that between the centering element and the end of the rotating shaft there is provided a guide disk, which extends substantially orthogonally with respect to the rotating shaft, the end of the rotating shaft the guide disk and the centering element having guide means such that the centering element can be displaced with respect to the guide disk only in a first direction, and the guide disk can be displaced with respect to the rotating shaft only in a second direction orthogonal to the first direction.

10. The device for the precision rotation of samples as claimed in claim 9, characterized in that the guide means comprise pins fixed to the guide disk on the rotating shaft side and on the centering element side and substantially at the center of said disk, and also grooves, at the end of the rotating shaft and in the region of the centering element on the guide disk side, to accommodate the pins, the grooves extending orthogonally with respect to each other and orthogonally with respect to the rotating shaft when the guide means are fitted.

11. The device for the precision rotation of samples as claimed in claim 1, characterized in that the sample holder is held on the centering element by vacuum, which is generated by a pump device connected to the centering element.

12. The device for the precision rotation of samples as claimed in claim 1 characterized in that it also contains an optical device for detecting the position of the beam and the position of the sample, comprising:
    a scintillator that can optionally be set up at the sample location, and
    a video microscope aimed at the sample location.

13. The device for the precision rotation of samples as claimed in claim 12, characterized in that the scintillator is fixed to a motorized displacement table.

14. The device for the precision rotation of samples as claimed in claim 12 characterized in that the scintillator is coupled to a photodiode by means of an optical waveguide.

15. The device for the precision rotation of samples as claimed in claim 12 characterized in that the video microscope is aimed at the sample location coaxially with respect to the beam.

16. The device for the precision rotation of samples as claimed in claim 12 characterized in that the image registered by the video microscope is fed to a computer for automatic beam localization and sample adjustment.

17. The device for the precision rotation of samples as claimed in claim 15, characterized in that the video microscope is arranged in the forward direction in extension of the beam.

18. The device for the precision rotation of samples as claimed in claim 15, characterized in that the video microscope is aimed, with an orientation of 90E with respect to the beam, at a mirror which is oriented at 45E with respect to the beam and is penetrated by the latter through a hole provided in the mirror.

19. The device for the precision rotation of samples as claimed in claim 15, characterized in that an objective of the video microscope is provided with a coaxial hole, through which the beam runs before reaching the sample.

20. The device for the precision rotation of samples as claimed in claim 1 characterized in that the rotating shaft and the components connected thereto are fixed to a diffractometer table or a motorized tilting device.

21. The device for the precision rotation of samples as claimed in claim 1 characterized in that it comprises further motorized displacement tables for the introduction of beam stops, and/or beam tubes and the like into the beam.

22. The device for the precision rotation of samples as claimed in claim 1 characterized in that it also comprises means for attaching a sample surround.

23. The device for the precision rotation of samples as claimed in claim 1 characterized in that the rotating shaft is mounted using ball bearings (24a,24b).

24. The device for the precision rotation of samples as claimed in claim 1 characterized in that the rotating shaft is mounted using air bearings.

25. The device according to claim 1, wherein the centering element is generally in the shape of a disk.

26. A device for the precision rotation of samples on a diffractometer, comprising:
    a motor driven rotating shaft;
    a centering element which is held at one end of the rotating shaft and can be displaced in a plane orthogonal to the axis of rotation of the rotating shaft;
    a sample holder, which is fixed to the centering element or integral with the latter and which moves with the centering element when the centering element is displaced in the plane orthogonal to the axis of rotation of the rotating shaft, for holding a sample substantially centrally with respect to the axis of rotation in an X-ray or synchrotron radiation beam;
    at least one micrometer finger which is arranged in the region of the centering element in order to displace the centering element in a plane orthogonal to the axis of rotation of the rotating shaft and can be positioned orthogonally with respect to the axis of rotation of the rotating shaft by means of a micrometer finger drive device.

27. The device for the precision rotation of samples as claimed in claim 26, further comprising a device for detecting the instantaneous clear distance, or possibly zero distance, between the micrometer finger and the centering element.

28. The device for the precision rotation of samples as claimed in claim 26, characterized in that the centering element is held magnetically on the rotating shaft.

29. The device for the precision rotation of samples as claimed in claim 26, further comprising an encoder for determining the rotational position of the rotating shaft, possibly an electric motor driving the rotating shaft.

30. The device according to claim 26, wherein the centering element is generally in the shape of a disk.

31. A device for the precision rotation of samples, comprising:
    a motor driven rotating shaft having an axis of rotation;
    a centering element coupled to an end of the rotating shaft so that the centering element rotates with the rotating shaft, wherein the centering element is movable relative to the rotating shaft in a plane perpendicular to the axis of rotation of the rotating shaft;
    sample holding means, connected to the centering element so that the sample holding means moves with the centering element when the centering element is displaced in the plane perpendicular to the axis of rotation of the rotating shaft, for holding a sample; and
    moving means for moving the centering element in a direction perpendicular to the axis of rotation of the rotating shaft.

32. The device of claim 31, wherein the centering element is coupled to the end of the rotating shaft though a magnetic force.

33. The device of claim 31, wherein the centering element has a first side and a second side, the first side facing the end of the rotating shaft and the second side facing in the opposite direction, wherein the sample holding means is connected to the second side of the centering element.

34. The device of claim 31, wherein the means for moving the centering element comprises a micrometer drive device for moving a micrometer finger having an end facing the centering element.

35. The device of claim 34, further comprising detection means for detecting the distance between the end of the micrometer finger and the centering element.

36. The device of claim 34, wherein the detection means comprises a capacitance sensor arranged at the end of the micrometer finger facing the centering element.

37. The device of claim 31, further comprising a means for determining the rotational position of the rotating shaft.

38. The device according to claim 31, wherein the centering element is generally in the shape of a disk.

39. The device of claim 31, further comprising a guide disk that is positioned between the end of the rotating shaft and the centering element.

40. The device of claim 39, further comprising means for ensuring that the guide disk can be displaced relative to the rotating shaft only upward or downward.

41. The device of claim 40, wherein the guide means comprises a pin fixed to a side of the guide disk facing the end of the rotating shaft.

* * * * *